(12) United States Patent
Krueger et al.

(10) Patent No.: US 11,051,746 B2
(45) Date of Patent: Jul. 6, 2021

(54) ATRIAL FIBRILLATION DETECTION USING VENTRICULAR RATE VARIABILITY

(71) Applicant: Cardiac Pacemakers, Inc., St. Paul, MN (US)

(72) Inventors: Jonathan Walter Krueger, New Richmond, WI (US); Deepa Mahajan, Roseville, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 37 days.

(21) Appl. No.: 14/825,669

(22) Filed: Aug. 13, 2015

(65) Prior Publication Data

US 2016/0045125 A1    Feb. 18, 2016

Related U.S. Application Data

(60) Provisional application No. 62/037,348, filed on Aug. 14, 2014.

(51) Int. Cl.
*A61B 5/361* (2021.01)
*G16H 50/20* (2018.01)
(Continued)

(52) U.S. Cl.
CPC .......... *A61B 5/361* (2021.01); *A61B 5/02405* (2013.01); *A61B 5/316* (2021.01);
(Continued)

(58) Field of Classification Search
CPC ... A61B 5/024; A61B 5/02405; A61B 5/0245; A61B 5/04012; A61B 5/0402;
(Continued)

(56) References Cited

U.S. PATENT DOCUMENTS 5,562,709 A    10/1996    White
5,622,178 A *   4/1997    Gilham .............. G06K 9/00557
                                                                600/515
(Continued)

FOREIGN PATENT DOCUMENTS

AU    2015301633 B2    8/2018
CN    1829554 A    9/2006
(Continued)

OTHER PUBLICATIONS

Esperer et al. "Cardiac arrhythmias imprint specific signatures on Lorenz plots". Ann Noninvasive Electrocardiol. Jan. 2008;13(1):44-60. doi: 10.1111/j.1542-474X.2007.00200.x.*
(Continued)

*Primary Examiner* — Eugene T Wu
(74) *Attorney, Agent, or Firm* — Schwegman Lundberg & Woessner, P.A.

(57) ABSTRACT

Atrial fibrillation information can be determined from ventricular information or a ventricular location, such as using ventricular rate variability. An ambulatory medical device can receive indications of pairs of first and second ventricular rate changes of three temporally adjacent ventricular heart beats. A first count of instances of the pairs meeting a combined rate change magnitude characteristic and a second count of instances of the pairs in which both of the first and second ventricular rate changes are negative can be used to provide atrial fibrillation information.

18 Claims, 7 Drawing Sheets

(51) Int. Cl.
*A61B 5/024* (2006.01)
*A61B 5/316* (2021.01)
*A61B 5/00* (2006.01)
*A61B 5/366* (2021.01)

(52) U.S. Cl.
CPC .............. *G16H 50/20* (2018.01); *A61B 5/366* (2021.01); *A61B 5/7203* (2013.01); *A61B 5/7264* (2013.01); *A61B 5/7278* (2013.01)

(58) Field of Classification Search
CPC ... A61B 5/0432; A61B 5/04325; A61B 5/044; A61B 5/0452; A61B 5/04525; A61B 5/046; A61B 5/7203; A61B 5/7221; A61B 5/7235; A61B 5/7239; A61B 5/7246; A61B 5/7282; A61B 5/746
See application file for complete search history.

(56) References Cited

U.S. PATENT DOCUMENTS

| | | |
|---|---|---|
| 6,490,479 B2 | 12/2002 | Bock |
| 6,931,273 B2 | 8/2005 | Groenewegen et al. |
| 7,031,765 B2 | 4/2006 | Ritscher et al. |
| 7,115,096 B2 | 10/2006 | Siejko et al. |
| 7,308,306 B1 | 12/2007 | Park et al. |
| 7,353,057 B2 * | 4/2008 | Schiessle .......... A61B 5/02405 600/518 |
| 7,412,282 B2 | 8/2008 | Houben |
| 7,566,308 B2 | 7/2009 | Stahmann |
| 7,596,405 B2 | 9/2009 | Kurzweil et al. |
| 7,634,310 B2 | 12/2009 | Lee et al. |
| 7,657,307 B2 | 2/2010 | Van Dam et al. |
| 7,899,531 B1 | 3/2011 | Benser et al. |
| 7,904,142 B2 | 3/2011 | Kim et al. |
| 7,970,468 B1 | 6/2011 | Ostrow |
| 8,195,280 B2 | 6/2012 | Van Dam et al. |
| 8,560,058 B2 | 10/2013 | Babaeizadeh et al. |
| 8,639,316 B2 | 1/2014 | Sarkar |
| 9,999,368 B2 | 6/2018 | Perschbacher et al. |
| 10,485,442 B2 | 11/2019 | Krueger et al. |
| 10,542,902 B2 | 1/2020 | Perschbacher et al. |
| 10,617,320 B2 | 4/2020 | Mahajan et al. |
| 10,881,317 B2 | 1/2021 | Perschbacher et al. |
| 2001/0034539 A1 | 10/2001 | Stadler et al. |
| 2002/0065473 A1 * | 5/2002 | Wang .................. A61B 5/02405 600/518 |
| 2004/0092836 A1 * | 5/2004 | Ritscher ............... A61B 5/0464 600/518 |
| 2005/0080347 A1 * | 4/2005 | Sheth ..................... A61B 5/046 600/515 |
| 2005/0154421 A1 | 7/2005 | Ousdigian |
| 2006/0247548 A1 * | 11/2006 | Sarkar .................. A61B 5/0464 600/515 |
| 2007/0038253 A1 | 2/2007 | Kim et al. |
| 2007/0100248 A1 * | 5/2007 | Van Dam ........... A61B 5/02405 600/515 |
| 2008/0161703 A1 * | 7/2008 | Houben ............. A61B 5/02405 600/509 |
| 2009/0112110 A1 | 4/2009 | Zhang |
| 2010/0057152 A1 | 3/2010 | Kim et al. |
| 2010/0168597 A1 | 7/2010 | Kim et al. |
| 2010/0274149 A1 | 10/2010 | Li et al. |
| 2010/0305642 A1 | 12/2010 | Dong et al. |
| 2011/0152957 A1 | 6/2011 | Shaquer |
| 2012/0035489 A1 | 2/2012 | Dong et al. |
| 2012/0101541 A1 * | 4/2012 | Corbucci ............. A61B 5/0468 607/17 |
| 2012/0238891 A1 * | 9/2012 | Sarkar .................. A61B 5/0468 600/516 |
| 2012/0238892 A1 * | 9/2012 | Sarkar .................. A61B 5/0402 600/516 |
| 2013/0053914 A1 * | 2/2013 | Shome ............... A61N 1/36139 607/18 |
| 2013/0150911 A1 | 6/2013 | Perschbacher et al. |
| 2013/0296680 A1 | 11/2013 | Linker |
| 2015/0088216 A1 | 3/2015 | Gordon et al. |
| 2016/0287115 A1 | 10/2016 | Perschbacher et al. |
| 2017/0027462 A1 | 2/2017 | Mahajan et al. |
| 2018/0242869 A1 | 8/2018 | Perschbacher et al. |
| 2018/0256053 A1 | 9/2018 | Perschbacher et al. |

FOREIGN PATENT DOCUMENTS

| | | |
|---|---|---|
| CN | 101925381 A | 12/2010 |
| CN | 107529988 A | 1/2018 |
| CN | 107847746 A | 3/2018 |
| CN | 106659407 B | 4/2020 |
| CN | 107529988 B | 10/2020 |
| EP | 2407097 A1 | 1/2012 |
| EP | 3277372 B1 | 8/2019 |
| ES | 2749127 T3 | 3/2020 |
| JP | 2004524074 A | 8/2004 |
| JP | 2006524106 A | 10/2006 |
| JP | 2008539015 A | 11/2008 |
| JP | 2009089883 A | 4/2009 |
| JP | 2013535236 A | 9/2013 |
| JP | 2017527356 A | 9/2017 |
| JP | 2018511400 A | 4/2018 |
| JP | 6434129 B2 | 11/2018 |
| JP | 6525461 B2 | 5/2019 |
| WO | WO-200611885 A2 | 11/2006 |
| WO | WO-2013020710 A1 | 2/2013 |
| WO | WO-2016025704 A1 | 2/2016 |
| WO | WO-2016160674 A1 | 10/2016 |
| WO | WO-2017019178 A1 | 2/2017 |
| WO | WO-2017079245 A1 | 5/2017 |

OTHER PUBLICATIONS

"International Application Serial No. PCT/US2015/045042, International Search Report dated Oct. 27, 2015", 6 pgs.

"International Application Serial No. PCT/US2015/045042, Written Opinion dated Oct. 27, 2015", 9 pgs.

"International Application Serial No. PCT/US2016/024463, International Search Report dated Jun. 17, 2016", 6 pgs.

"International Application Serial No. PCT/US2016/024463, Written Opinion dated Jun. 17, 2016", 6 pgs.

Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.

Tateno, K, et al., "Automatic detection of atrial fibrillation using the coefficient of variation and density histograms of RR and RR intervals", Medical and Biological Engineering and Computing, vol. 39, No. 6,, (Nov. 1, 2011), 664-671.

"U.S. Appl. No. 15/082,440, Corrected Notice of Allowance dated Feb. 9, 2018", 5 pgs.

"U.S. Appl. No. 15/082,440, Examiner Interview Summary dated Sep. 6, 2017", 2 pgs.

"U.S. Appl. No. 15/082,440, Non Final Office Action dated Jun. 21, 2017", 9 pgs.

"U.S. Appl. No. 15/082,440, Notice of Allowance dated Jan. 18, 2018", 8 pgs.

"U.S. Appl. No. 15/082,440, Notice of Allowance dated Sep. 25, 2017", 10 pgs.

"U.S. Appl. No. 15/082,440, Response filed Sep. 5, 2017 to Non Final Office Action dated Jun. 21, 2017", 14 pgs.

"U.S. Appl. No. 15/175,151, Advisory Action dated Sep. 12, 2019", 3 pgs.

"U.S. Appl. No. 15/175,151, Advisory Action dated Oct. 2, 2018", 3 pgs.

"U.S. Appl. No. 15/175,151, Advisory Action dated Oct. 23, 2019", 4 pgs.

"U.S. Appl. No. 15/175,151, Examiner Interview Summary dated Jan. 21, 2020", 3 pgs.

"U.S. Appl. No. 15/175,151, Final Office Action dated Jul. 5, 2019", 8 pgs.

(56) References Cited

OTHER PUBLICATIONS

"U.S. Appl. No. 15/175,151, Final Office Action dated Aug. 2, 2018", 10 pgs.
"U.S. Appl. No. 15/175,151, Non Final Office Action dated Feb. 23, 2018", 10 pgs.
"U.S. Appl. No. 15/175,151, Non Final Office Action dated Dec. 31, 2018", 8 pgs.
"U.S. Appl. No. 15/175,151, Notice of Allowance dated Dec. 4, 2019", 7 pgs.
"U.S. Appl. No. 15/175,151, Response filed Jan. 23, 2018 to Restriction Requirement dated Dec. 7, 2017", 9 pgs.
"U.S. Appl. No. 15/175,151, Response filed May 14, 2018 to Non Final Office Action dated Feb. 23, 2018", 14 pgs.
"U.S. Appl. No. 15/175,151, Response filed Sep. 3, 2019 to Final Office Action dated Jul. 5, 2019", 12 pgs.
"U.S. Appl. No. 15/175,151, Response filed Sep. 25, 2018 to Final Office Action dated Aug. 2, 2018", 11 pgs.
"U.S. Appl. No. 15/175,151, Response filed Oct. 7, 2019 to Advisory Action dated Sep. 12, 2019", 13 pgs.
"U.S. Appl. No. 15/175,151, Response filed Mar. 25, 2019 to Non Final Office Action dated Dec. 31, 2018", 11 pgs.
"U.S. Appl. No. 15/175,151, Restriction Requirement dated Dec. 7, 2017", 6 pgs.
"U.S. Appl. No. 15/175,151,Pre-Appeal Brief Request for Review filed Nov. 4, 2019", 5 pgs.
"U.S. Appl. No. 15/341,565, Non Final Office Action dated Mar. 6, 2019", 12 pgs.
"U.S. Appl. No. 15/341,565, Notice of Allowance dated Jul. 26, 2019", 8 pgs.
"U.S. Appl. No. 15/341,565, Response filed Jun. 6, 2019 to Non Final Office Action dated Mar. 6, 2019", 10 pgs.
"U.S. Appl. No. 15/341,565, Response filed Dec. 10, 2018 to Restriction Requirement dated Oct. 15, 2018", 8 pgs.
"U.S. Appl. No. 15/341,565, Restriction Requirement dated Oct. 15, 2018", 6 pgs.
"U.S. Appl. No. 15/901,336, Non Final Office Action dated Jun. 21, 2020", 8 pgs.
"U.S. Appl. No. 15/901,336, Non Final Office Action dated Apr. 23, 2020", 7 pgs.
"U.S. Appl. No. 15/901,336, Response filed Feb. 27, 2020 to Non Final Office Action dated Jan. 21, 2020", 8 pgs.
"U.S. Appl. No. 15/967,326, Advisory Action dated Mar. 14, 2019", 3 pgs.
"U.S. Appl. No. 15/967,326, Final Office Action dated Jan. 3, 2019", 11 pgs.
"U.S. Appl. No. 15/967,326, Final Office Action dated Aug. 7, 2019", 6 pgs.
"U.S. Appl. No. 15/967,326, Non Final Office Action dated Apr. 18, 2019", 9 pgs.
"U.S. Appl. No. 15/967,326, Non Final Office Action dated Jun. 29, 2018", 9 pgs.
"U.S. Appl. No. 15/967,326, Notice of Allowance dated Jun. 16, 2019", 7 pgs.
"U.S. Appl. No. 15/967,326, Response filed Feb. 21, 2019 to Final Office Action dated Jan. 3, 2019", 11 pgs.
"U.S. Appl. No. 15/967,326, Response filed Jul. 18, 2019 to Non Final Office Action dated Apr. 18, 2019", 8 pgs.
"U.S. Appl. No. 15/967,326, Response filed Aug. 20, 2019 to Final Office Action dated Aug. 7, 2019", 8 pgs.
"U.S. Appl. No. 15/967,326, Response filed Sep. 24, 2018 to Non Final Office Action dated Jun. 29, 2018", 13 pgs.
"Application Serial No. PCT/US2016/036146, Invitation to Pay Add'l Fees and Partial Search Report dated Oct. 6, 2016", 7 pgs.
"Australian Application Serial No. 2015301633, First Examiners Report dated Sep. 7, 2017", 3 pgs.
"Australian Application Serial No. 2015301633, Response filed Mar. 21, 2018 to First Examiners Report dated Sep. 7, 2017", 14 pgs.
"Chinese Application Serial No. 201580047246.7, Office Action dated Mar. 6, 2019", w/ English Translation, 19 pgs.
"Chinese Application Serial No. 201580047246.7, Office Action dated Sep. 19, 2019", W/ English Translation, 10 pgs.
"Chinese Application Serial No. 201580047246.7, Response Filed Jul. 22, 2019 to Office Action dated Mar. 6, 2019", w/English Claims, 17 pgs.
"Chinese Application Serial No. 201580047246.7, Response filed Dec. 4, 2019 to Office Action dated Sep. 19, 2019", w/ English claims, 13 pgs.
"Chinese Application Serial No. 201580047246.7, Response to Examiner Telephone Interview filed Dec. 18, 2019", w/ English claims, 10 pgs.
"Chinese Application Serial No. 201680018682.6, Office Action dated May 26, 20", With English Translation, 8 pgs.
"Chinese Application Serial No. 201680018682.6, Response filed Apr. 10, 2020 to Office Action dated Dec. 2, 2019", w/ English Claims, 14 pgs.
"European Application Serial No. 15757059.9, Response filed Sep. 26, 2017 to Communication Pursuant to Rules 161(1) and 162 EPC dated Mar. 21, 2017", 18 pgs.
"European Application Serial No. 16715709.8, Response filed Jun. 27, 2018 to Communication Pursuant to Rules 161(1) and 162 EPC dated Dec. 7, 2017", 28 pgs.
"International Application Serial No. PCT/US2016/024463, International Preliminary Report on Patentability dated Oct. 12, 2017", 8 pgs.
"International Application Serial No. PCT/US2016/036146, International Preliminary Report on Patentability dated Feb. 8, 2018", 12 pgs.
"International Application Serial No. PCT/US2016/036146, International Search Report dated Dec. 7, 2016", 5 pgs.
"International Application Serial No. PCT/US2016/036146, Written Opinion dated Dec. 7, 2016", 10 pgs.
"International Application Serial No. PCT/US2016/060050, International Search Report dated Feb. 6, 2017", 4 pgs.
"International Application Serial No. PCT/US2016/060050, Written Opinion dated Feb. 6, 2017", 5 pgs.
"Japanese Application Serial No. 2017-508064, Office Action dated Mar. 6, 2018", With English Translation, 4 pgs.
"Japanese Application Serial No. 2017-508064, Response filed May 30, 2018 to Office Action dated Mar. 6, 2018", w/ English claims, 10 pgs.
"Japanese Application Serial No. 2017-550731, Notification of Reasons for Refusal dated Dec. 18, 2018", w/ English summary, 6 pgs.
"Japanese Application Serial No. 2017-550731, Office Action dated Sep. 4, 2018", w/ English translation (machine), 8 pgs.
"Japanese Application Serial No. 2017-550731, Response filed Mar. 15, 2019 to Notification of Reasons for Refusal dated Dec. 18, 2018", w/ English claims, 6 pgs.
"Japanese Application Serial No. 2017-550731, Response filed Nov. 28, 2018 to Office Action dated Sep. 4, 2018", w/ English claims, 8 pgs.
Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.
"U.S. Appl. No. 15/901,336, Notice of Allowance dated Sep. 9, 2020", 7 pgs.
"U.S. Appl. No. 15/901,336, Response filed Jul. 23, 2020 to Non Final Office Action dated Apr. 23, 20", 8 pgs.
"Chinese Application Serial No. 201680018682.6, Response filed Aug. 7, 2020 to Office Action dated May 26, 2020", w/ English claims, 12 pgs.
"European Application Serial No. 15757059.9, Communication Pursuant to Article 94(3) EPC dated Jul. 2, 2020", 5 pgs.
"European Application Serial No. 15757059.9, Response filed Nov. 12, 2020 to Communication Pursuant to Article 94(3) EPC dated Jul. 2, 2020", 7 pgs.

* cited by examiner

| $\Delta R_{i,i+1}$ | $\Delta R_{i+1,i+2}$ | $\Delta R_{i+2,i+3}$ | $\Delta R_{i+3,i+4}$ | |
|---|---|---|---|---|
| $X_1$ | $Y_1$ | — | — | 402 |
| — | $X_2$ | $Y_2$ | — | 403 |
| — | — | $X_3$ | $Y_3$ | |

ATRIAL FIBRILLATION DETECTION USING VENTRICULAR RATE VARIABILITY

CLAIM OF PRIORITY

This application claims the benefit of priority under 35 U.S.C. § 119(e) of U.S. Provisional Patent Application Ser. No. 62/037,348, filed on Aug. 14, 2014, which is herein incorporated by reference in its entirety.

BACKGROUND

Atrial fibrillation (AF) is a common cardiac arrhythmia. AF is a disorganized atrial tachyarrhythmia in which a normal regular sinus rhythm is overwhelmed by uncoordinated electrical pulses originating from regions in or near an atrium. This can lead to irregular conductions to ventricles, thereby causing inappropriately fast and irregular heart rates. Paroxysmal AF may last from minutes to days before self-terminating. Persistent AF may last for over a week and may need medication, cardioversion, or other treatment to revert to normal sinus rhythm. Permanent AF generally cannot be restored with treatment. Persistent AF may become more frequent and may evolve into permanent AF. AF can be symptomatic or asymptomatic. Some consequences of AF may include palpitations, increased risk of thromboembolism (AF is associated with over 120,000 strokes per year), and development or progression of congestive heart failure (CHF).

CHF (also referred to as "heart failure" or "HF") affects over five million people in the United States alone. CHF may reduce the pumping power of the heart. This may result in the inability to deliver enough blood to meet the demands of peripheral tissue. A CHF patient may have an enlarged heart with weakened cardiac muscles, which may result in reduced cardiac muscle contractility and poor cardiac output of blood. CHF may affect the left side, right side, or both sides of the heart, which may result in non-simultaneous contractions of the left and right ventricles, referred to as dyssynchrony. This dyssynchrony may decrease the pumping efficiency of the heart.

There is a pathophysiological relationship between AF and CHF. Many CHF patients may experience AF or other types of atrial tachyarrhythmias. CHF can increase the risk for developing AF. Increased severity of CHF in patients may result in increased prevalence of AF.

OVERVIEW

Ambulatory medical devices (AMDs) can be used for monitoring cardiac activity in a patient and detect cardiac conditions. Examples of AMDs can include subcutaneous and other implantable medical devices (IMDs), and external medical devices. The implantable or other ambulatory medical devices can include one or more physiologic or other sensors, such as can be configured to sense cardiac activity, or one or more other characteristics such as can be associated with a subject's cardiac condition.

The present inventors have recognized, among other things, that a problem to be solved can include detecting AF using ventricular information or from a ventricular location, such as using ventricular rate variability. The present subject matter can help provide a solution to this problem, such as can include determining first and second indications of AF from ventricular information or from a ventricular location, such as to provide information about atrial fibrillation of a patient.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document. Such embodiments are demonstrative and not intended to be exhaustive or exclusive embodiments of the present apparatuses, systems, or methods.

DETAILED DESCRIPTION

Disclosed herein are apparatuses, systems, and methods such as can be used for detecting atrial fibrillation (AF), such as can include (or consist of) using ventricular information or information obtained from a ventricular location. By monitoring a patient's ventricular heart rhythm activity such as described herein, atrial fibrillation information can be detected and monitored.

Figure 1:
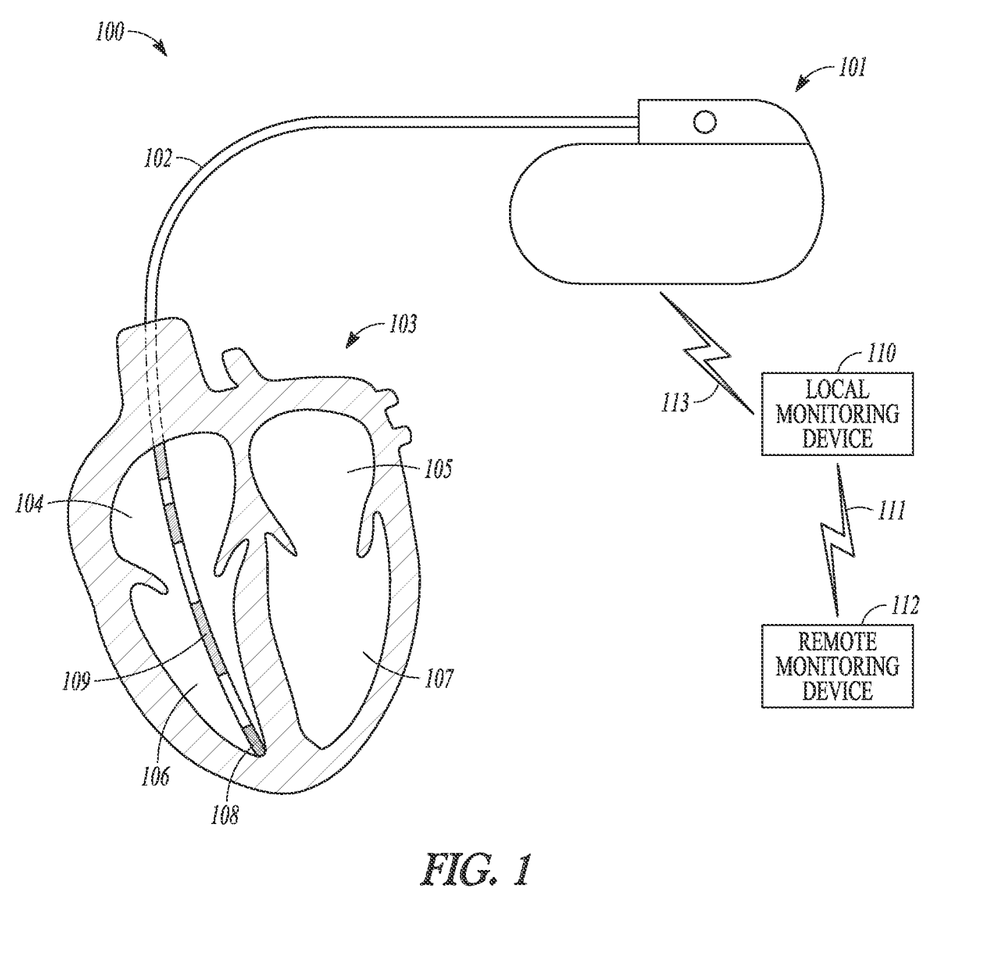
FIG. 1 illustrates an example of portions of an example of a system that can include an implantable medical device (IMD) or other ambulatory medical device.

FIG. 1 illustrates an example of portions of a system 100. The system 100 can include an ambulatory medical device, such as an implantable medical device 101. The implantable medical device 101 can be coupled, such as by one or more leads 102, to a desired location such as a heart 103. The heart 103 includes a right atrium 104, a left atrium 105, a right ventricle 106, and a left ventricle 107. The lead 102 can include one or more electrodes (e.g., electrical contacts, such as a tip electrode 108 or a coil electrode 109) that can be sized, shaped, spaced, or otherwise configured to be located in or in association with a ventricle 106, 107 of the heart 103. The implantable medical device 101 can be configured to communicate to a monitoring device or multiple monitoring devices (e.g., a local monitoring device 110 or a remote monitoring device 112). This can include using one or more communication links (e.g., communication links 111 or 113). The communication links can include wired or wireless transmitter, receiver, or transceiver circuits, such as at each end of the communication link.

The system 100 can additionally or alternatively include an ambulatory (e.g., a wearable or implantable) or a non-ambulatory device (e.g., a stationary electrocardiogram monitoring device) that can include a physiologic sensor circuit. The physiologic sensor circuit can be configured to sense at least one physiological signal of a patient (e.g., intrinsic electrical cardiac signal, heart sound, pressure, temperature, mechanical indications of heart beats, or other physiologic information). In addition to (or as alternative to) the transvenous lead 102, the system 100 can include a subcutaneous electrode or electrode array. The subcutaneous electrode or electrode array can be located on the implantable or other ambulatory medical device, or on a lead extending from the implantable or other ambulatory medical device.

The local monitoring device 110 or remote monitoring device 112 can be configured to include one or more circuits that perform at least some portion of the techniques described herein. The system 100 can be configured to operate in real time or off-line such as operating on previously collected and stored data.

Figure 2:
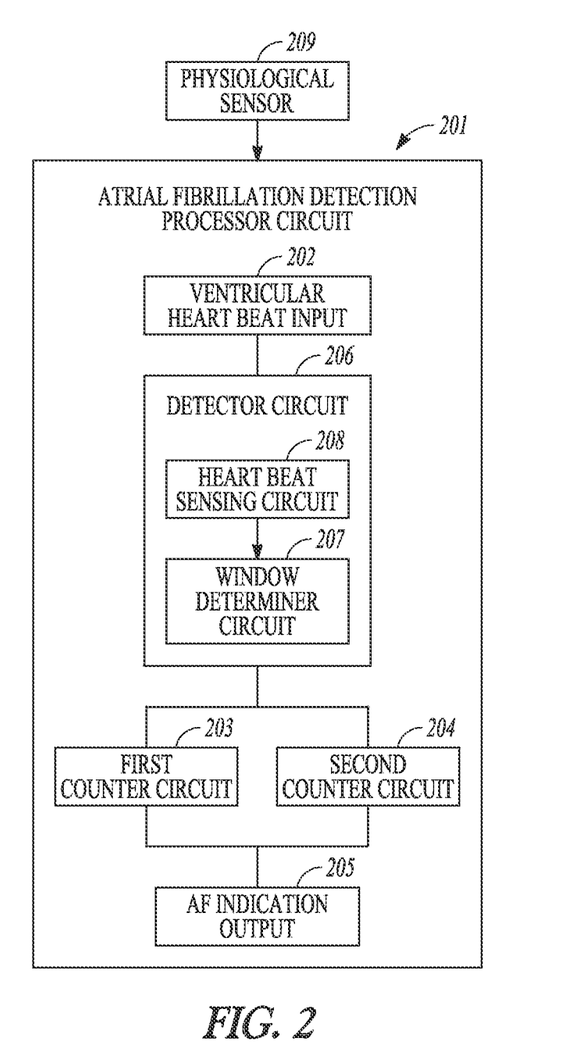
FIG. 2 illustrates an example of an atrial fibrillation detection processor circuit.

FIG. 2 illustrates an example of an AF detection processor circuit 201, such as can be included in the ambulatory or other implantable medical device 101 or elsewhere in the system 100. One or more portions of the AF detection processor circuit 201 can be included in an external system, such as in an ambulatory or other patient monitor, such as can be configured to provide patient arrhythmic information to an end-user. Such patient arrhythmic information can include information to indicate a relative amount of AF occurring during a period of time.

The AF detection processor circuit 201 can include an application-specific integrated circuit (ASIC) constructed to perform one or more particular functions, or can include a hardware circuit that can be programmed to perform such one or more functions. Such a programmed hardware circuit can include a microprocessor, a microcontroller, or a programmable logic circuit, or a portion of one or more of these. In an example, the AF detection processor circuit 201 can include a ventricular heart beat input 202, a first counter circuit 203, a second counter circuit 204, an AF indication output 205, a detector circuit 206 that can be configured to detect valid windows, a window determiner circuit 207 that can be configured to declare windows to be valid, and a heart beat sensing circuit 208 that can be configured to declare beats to valid.

The AF detection processor circuit 201 can be coupled to a physiological sensor 209. The physiological sensor 209 can be configured to sense cardiac information indicative of a heart rate of the patient. The physiological sensor 209 can include one or more implantable sensors, wearable sensors, or other ambulatory cardiac activity sensors that can be configured to sense cardiac activity. The physiological sensor 209 can be configured to sense the heart rate information based on electrical, mechanical, or electromechanical cardiac activity, such as pressure, impedance, acoustics, or any combination thereof. In an example, the physiological sensor can include or be coupled to the tip electrode 108.

Figure 3A:
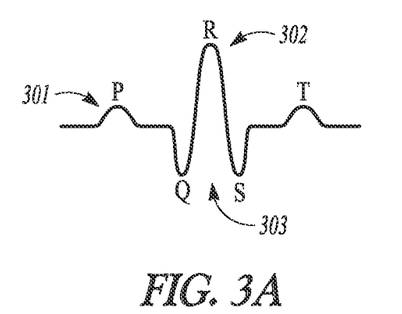
FIG. 3A is a pictorial example of an indication of a QRS complex of a cardiac cycle.

FIG. 3A is a pictorial example of a QRS complex 303 of an intrinsic electrical cardiac signal 301. An electrocardiogram (EKG or ECG) represents an intrinsic electrical cardiac signal, which includes atrial and ventricular depolarizations. The ECG can include recurring cardiac cycles that can respectively include a P-wave, the QRS complex 303, the R-wave 302, and a T wave.

The AF detection processor circuit 201 can include or be coupled to a timer circuit. The timer circuit can be configured to measure time interval duration between detected paced or sensed events. An example of such a measured time interval can be an R-R interval between successive (e.g., temporally adjacent) sensed QRS complexes 303 associated with respective successive ventricular depolarizations associated with respective ventricular heart beats. Another example of such a measured time interval can be a window, e.g., beginning with and concluding with a ventricular depolarization but including more than two successive (e.g., temporally adjacent) ventricular heart beats. The AF detection processor circuit can include or be coupled to a memory circuit, a communication circuit, or a signal processor circuit that can be configured to perform digital or other signal processing or to analyze information from one or more physiological signals such as from one or more sensors.

Figure 3B:
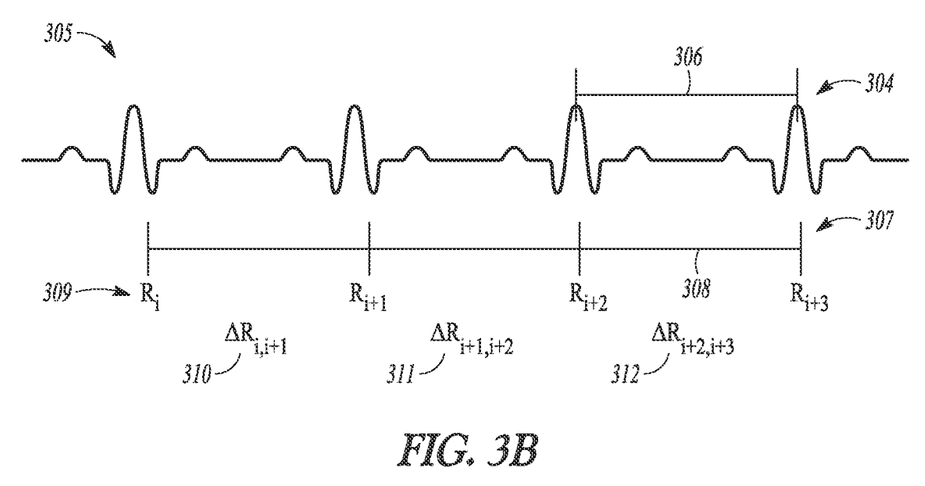
FIG. 3B is a pictorial example of an indication of a heart rhythm and heart rhythm parameters.

FIG. 3B is a pictorial example of an indication of a heart rhythm 305 and heart rhythm parameters. The QRS complex 303 occurs recurrently in the heart rhythm 305 with each cardiac cycle. An R-wave 304 can be used as a fiducial marker to represent a time of occurrence of a ventricular heart beat. Temporally adjacent R-waves 304 can be used to define the length of an R-R interval 306. The R-R interval 306 duration can vary during exercise and even when the patient is at rest during normal sinus rhythm of the heart, and can also vary during a cardiac arrhythmia.

A representative time line 307 of the heart rhythm 305 can be used to illustrate conceptually how the AF detection processor circuit can be used to analyze heart activity. A ventricular heart rate, $R_i$, 309 can represent the then-current heart rate at R-waves 304. The ventricular heart rate can be calculated using the R-R interval 306 duration by Equation 1.

$$\text{Rate}_{ventricle}(\text{in beats per minute})=60{,}000/(R\text{-}R \text{ interval, in milliseconds}) \quad \text{(Eq. 1)}$$

A ventricular rate change 310-312 can be determined for two temporally adjacent ventricular heart beats, and can be assigned to one of these two adjacent ventricular heart beats. For example, an R-R interval 308 that begins with $R_{i+2}$ and ends with $R_{i+3}$ can correspond to the ventricular rate change, $\Delta R_{i+2,i+3}$, 312. The representative time line 307 depicts two pairs of ventricular rate changes. A first pair, ($\Delta R_{i,i+1}$, $\Delta R_{i+1,i+2}$) 310-311 corresponds to three temporally adjacent heart beats, $R_i$ through $R_{i+2}$. A second pair, ($\Delta R_{i+1,i+2}$, $\Delta R_{i+2,i+3}$) 311-312 corresponds to three temporally adjacent heart beats $R_{i+1}$ through $R_{i+3}$.

Figure 3C:
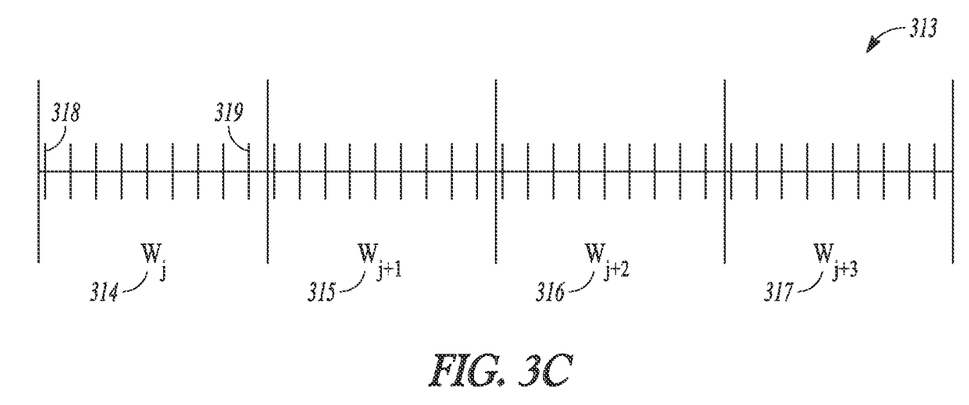
FIG. 3C illustrates an example of windows such as can be used with an indication of a heart rhythm.

FIG. 3C illustrates an example of windows including respective indications of a heart rhythm. A window timeline 313 can be used to illustrate how the AF detection circuit can be used to analyze heart activity. The window timeline 313 can include multiple windows 314-317. An individual window 314-317 can include multiple temporally adjacent ventricular heart beats (e.g., a first ventricular heart beat 318 through a last ventricular heart beat 319). In an example, the windows 314-317 can be temporally non-overlapping, and the individual windows can each include the same number, N, of temporally adjacent ventricular beats (e.g., N can be 100 adjacent cycles, 192 adjacent cycles, or another value). In an example, the windows 314-317 can each be the same duration such as measured in time (e.g., 120 seconds or another time value). For example, the first ventricular heart beat 318 in the window, $W_j$ 314, can be the first beat upon which a pair of ventricular rate changes is based, and the last ventricular heart beat 319 can be the Nth beat upon which a pair of ventricular rate changes is based. In an example, the ventricular heart beats 318-319 in the individual windows 314-317 can provide information about ventricular heart rate and information about ventricular rate changes of three temporally adjacent heart beats. Thus, a window of N ventricular heart beats can correspond to N−1 ventricular rate changes. For example, three temporally adjacent ventricular heart beats can correspond to one pair of ventricular rate changes. Similarly, four temporally adjacent ventricular heart beats can correspond to two pairs of ventricular rate changes. The window determiner circuit 207 can be configured to determine such rate change information about multiple temporally adjacent ventricular heart beats corresponding to individual windows 314-317.

Figure 4A:
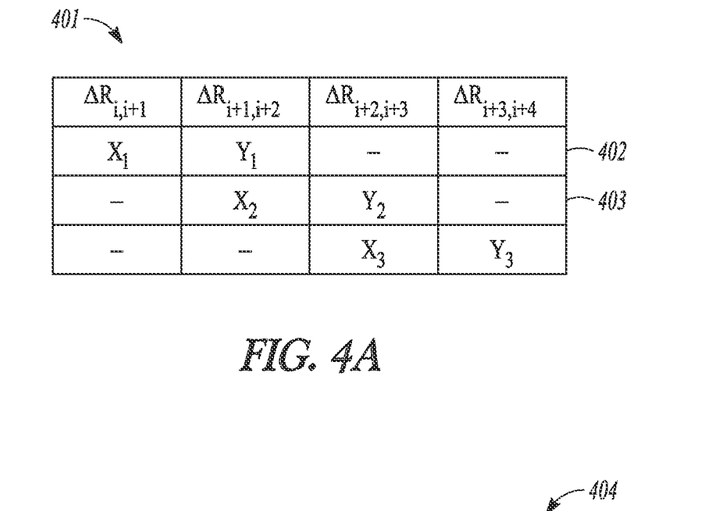
FIG. 4A illustrates an example of heart rhythm parameters.

FIG. 4A illustrates examples of heart rhythm parameters in a table 401 representing conceptual (not real data) information about ventricular rate change information. In an example, columns of the table 401 can list examples of the ventricular rate changes 310-312. In an example, rows of the table 401 can list examples of representations of pairs of ventricular rate changes as an abscissa and as an ordinate. In a first row 402, the ordinate representing the second ventricular rate change of a pair can correspond to the abscissa of a second row 403. The table 401 can be an optional way of conceptualizing the techniques discussed in this document, and the techniques discussed in this document can be carried out without the need to use tables such as the table 401.

Figure 4B:
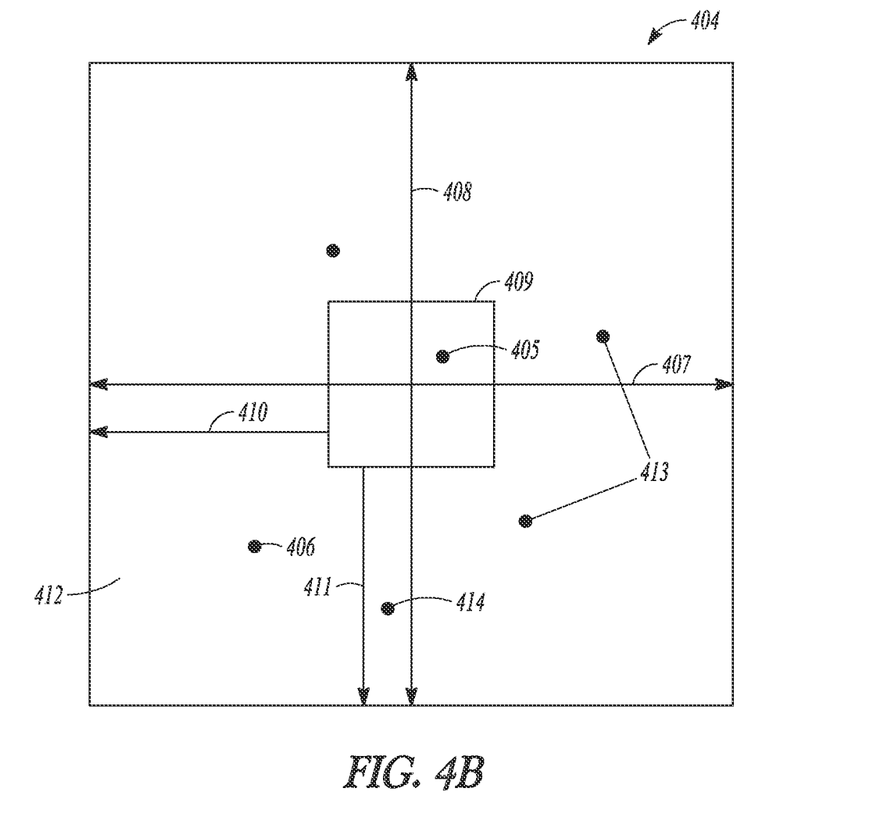
FIG. 4B illustrates an example of various regions on a rate-based scatter plot.

FIG. 4B illustrates an example of various regions on a rate-based scatter plot 404, which can be referred to as a Lorenz plot, such as can represent the ventricular rate change information such as described above. The rate-based scatter plot 404 can optionally be used to conceptualize the techniques discussed in this document, and the techniques discussed in this document can be carried out without the need to use two-dimensional or other plots, such as the rate-based scatter plot 404. A horizontal axis 407 of the scatter plot 404 can represent one ventricular rate change of a pair, and a vertical axis 408 of the scatter plot 404 can represent the other ventricular rate change of a pair. The horizontal axis 407 and vertical axis 408 can be measured in units of beats per minute (bpm). The information of the first row 402 can be represented as a point on the scatter plot 404, such that $X_1$ represents the abscissa and $Y_1$ represents the ordinate. The points 405-406, 413 represent conceptual (not real data) information about ventricular rate change information. One or more regions can be defined on the scatter plot 404, such as to impose one or more criteria on the points on the scatter plot 404, such as by counting those points that fall within a particular region, which can be further processed to provide useful information about AF, such as described further below.

A first region 409 can impose a "magnitude" criterion within the context of the scatter plot 404. Such a magnitude criterion can be represented on the scatter plot 404 so as to include and be centered at the origin of the scatter plot 404. For example, a "radial magnitude" criterion can be implemented using a first region 409 that can be represented as a circle on the scatter plot 404, such as centered at and including the origin of the scatter plot 404. A "component axis magnitude" criterion can be implemented using a first region 409 that can be represented as a square on the scatter plot 404, such as centered at and including the origin of the scatter plot 404. The "component axis magnitude" criterion need not impose an equal magnitude criterion on each component axis. For example, the "component axis magnitude" criterion can be implemented using a first region 409 that can be represented as a rectangle on the scatter plot 404, such as centered at and including the origin of the scatter plot 404. The first region 409 that can impose the "radial magnitude," the "component axis magnitude," or other "magnitude" criterion can include portions represented in all four quadrants of the scatter plot 404. A first point 405 can represent a pair of ventricular rate changes that occurs in the first region 409.

Magnitude criteria values of the first region 409 can be measured in units of beats per minute. For example, the "radial" magnitude criterion can take on a radius value, such as 4.5 bpm, or 5 bpm. The "component axis magnitude" criterion of the first region 409 can take on a side length value, such as 4.5 bpm or 2.8 bpm, and can be represented as a square (e.g., an equal magnitude value imposed on each component axis) or as a rectangle (e.g., different magnitude values are imposed opposite sides of the rectangle) on the scatter plot 404.

A second region 412 can impose a "double decrement" criterion within the context of the scatter plot 404, such that points on the scatter plot 404 that fall within the second region 412 can represent a pair of consecutive decreases in ventricular heart rate. The "double decrement" second region 412 can be represented entirely in the third quadrant of the scatter plot 404. The second region 412 can be defined so as to exclude the space on the scatter plot 404 within the first region 409, such that the second region 412 does not overlap with the first region 409 on the scatter plot 404. The second region 412 on the scatter plot 404 can include "component axis" limits, such as to define "noise margins" by which the second region 412 is separated from the axes of the scatter plot 404. For example, the second region 412 can include a vertical first limit 410 (e.g., a horizontal line occurring below the horizontal axis 407) on the scatter plot 404 and a horizontal second limit 411 (e.g. a vertical line occurring left of the vertical axis 408). The vertical first limit 410 and the horizontal second limit 411 can occur at the same distance from the axes 407-408 of the scatter plot 404 or can occur at different distances from the axes 407-408 (e.g., values such as 2.1 bpm, 3 bpm, or 3.5 bpm from the axes) of the scatter plot 404. A double-negative (e.g., third quadrant) point 406 can represent a pair of consecutive ventricular rate changes in which both the first ventricular rate change and the second ventricular rate change of the pair are negative. A double-negative point 406 can occur in the second region 412 on the scatter plot 404, or it can occur in the third quadrant but outside of the second region 412, or it can occur in the third quadrant but outside of both the second region 412 and the first region 409. Other points 413, 414 can fall on the scatter plot 404 outside of the first region 409 and outside the second region 412. The points on scatter plot 404 are illustrative, and are not based on real data.

The first counter circuit 203 can be configured to determine a first count of instances of pairs of first and second ventricular rate changes of three temporally adjacent ventricular heart beats that fall within the first region 409 (e.g., meeting the "magnitude" criterion). The second counter circuit 204 can be configured to determine a second count of instances of the pairs that fall within the second region 412 (e.g., meeting the "double-decrement" and "noise margin" criteria). The first and second counter circuits 203, 204 can determine the first and second counts, respectively, for individual windows 314-317, such that the AF detection processor circuit 201 can provide first or second count or other AF information for individual windows 314-317.

Figure 5:
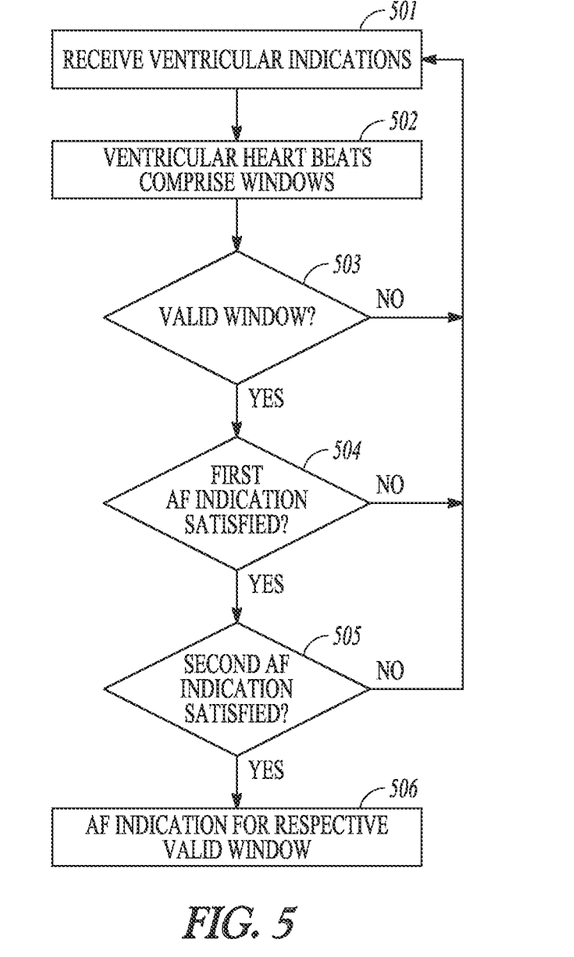
FIG. 5 illustrates an example of detecting atrial fibrillation

FIG. 5 illustrates an example of detecting AF. At 501, the AF detection processor circuit 201 can receive indications of heart activity from the physiological sensor 209, such as via a ventricular heart beat input 202 that can be coupled to a heart beat sensing circuit 208 that can be configured to receive indications of heart activity from the physiological sensor 209.

At 502, the window determiner circuit 207 can declare windows of ventricular heart beats to be valid based on whether the number of valid ventricular heart beats exceeds a specified minimum number of valid ventricular heart beats for that individual window. The window determiner circuit 207 can be configured to receive information about whether individual ventricular heart beats are valid from the heart beat sensing circuit 208 or the physiological sensor 209, either or both of which can be configured to declare whether individual ventricular heart beats are valid.

Figure 6:
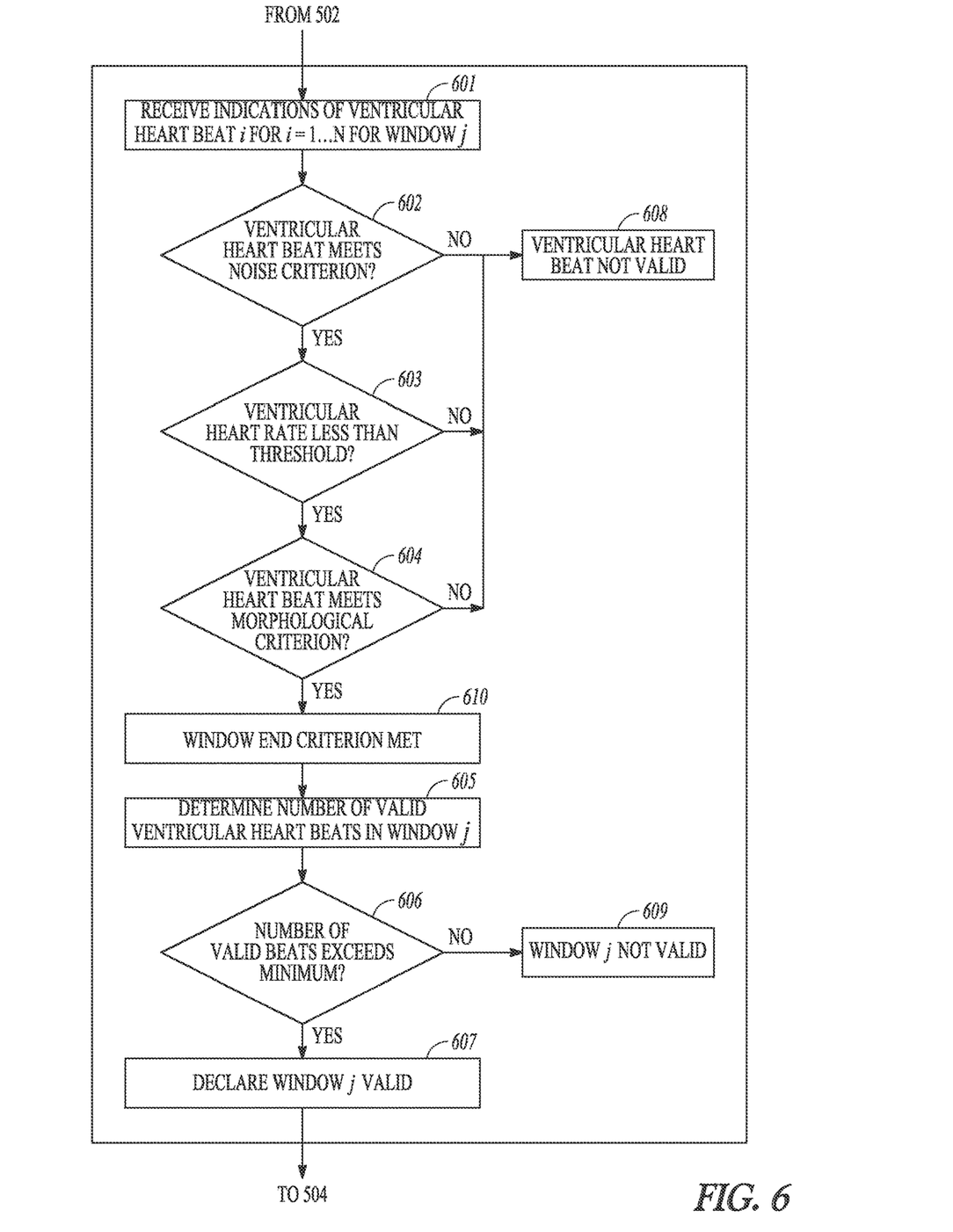
FIG. 6 illustrates an example of detecting atrial fibrillation using windows of heart beats.

FIG. 6 illustrates an example of detecting AF using windows of heart beats. At 601, the heart beat sensing circuit 208 can receive indications of ventricular heart beats.

At 602 the heart beat sensing circuit 208 can determine whether the ventricular heart beat indications meet a specified signal noise criterion. For example, the heart beat sensing circuit 208 can declare a ventricular heart beat to be invalid when a cardiac signal contains noise exceeding the specified signal noise criterion.

At 603 the heart beat sensing circuit 208 can determine whether the ventricular heart rate is less than a threshold rate. For example, the heart beat sensing circuit 208 can declare a ventricular heart beat invalid when the ventricular heart rate of the ventricular heart beat exceeds a specified "maximum rate" threshold rate (e.g., 170 bpm or 185 bpm).

At 604 the heart beat sensing circuit 208 can determine whether the ventricular heart beat meets a signal morphological criterion. For example, the heart beat sensing circuit 208 can declare a ventricular heart beat invalid when the ventricular heart beat does not sufficiently fit a template ventricular heart beat template. The fit can be based on one or more morphological characteristics such as signal amplitude, width, and shape of the QRS complex associated with the ventricular heart beat and that of the ventricular heart beat template.

The first and second counter circuits 203, 204 can be configured to count instances of pairs of consecutive ventricular rate changes for valid ventricular heart beats. For example, at 602-604, the heart beat sensing circuit 208 can determine whether ventricular heart beats are valid for use in the first and second counts that are associated with the first region 409 and the second region 412, respectively. If any criterion of 602-604 is not met, the ventricular heart beat can be declared invalid at 608 such as by the heart beat sensing circuit 208.

At 610, the end of the window can be determined such as by using the window determiner circuit 207. The end of the window can be determined such as by using a window end criterion (e.g., a specified number of temporally adjacent heart beats or a specified time value, such as described above).

At 605, the window determiner circuit 207 can determine the number of valid beats in a window when the individual ventricular heart beats in a window have been processed by the heart beat sensing circuit 208 to make its initial determination of whether heart beats are valid or invalid, such as described above.

At 606, the window determiner circuit 207 can determine whether the number of valid ventricular heart beats for the individual window exceeds a specified minimum number of valid ventricular heart beats for the individual window (e.g., a minimum value, such as 40 beat or 60 beats). When the specified minimum is exceeded, the window determiner circuit 207 can declare the individual window to be valid.

At 609 the window determiner circuit 207 can determine that the specified minimum number of valid ventricular heart beats for the particular window has not been met or exceeded, and the detector circuit 206 can be configured to declare the window to be invalid.

The AF detection processor circuit 201 can be configured to determine AF information. This can include determining one or more indications of AF (e.g., a count of windows that indicate AF for a given time period, or a total amount of time that AF has been deemed to have occurred for a given time period), for valid windows 503, 607. For example, at 504, the first counter circuit 203 can determine whether a first indication of AF is satisfied. This can include using the first count provided by the first counter circuit 203 to count instances of the pairs of ventricular rate changes that fall within the first region 409 (e.g., meet a "magnitude" criterion) over a window. Then, the first count, a, can be further processed, such as to determine an indication of the first count relative to the total number of instances of pairs in a window over which the first and second counts are determined, T, less the first count. The indication of the first count can be calculated using Equation 2.

$$\text{First Indication} = a/(T-a) \quad \text{(Eq. 2)}$$

At 505, the second counter circuit 204 can determine whether a second indication of AF is satisfied. The second indication of AF can be determined using the second count provided by the second counter circuit 204 to count instances of the pairs of ventricular rate changes that fall within the second region 412 over a window. Then, the second count, b, can be further processed, such as to determine an indication of the second count relative to the total number of instances of pairs in a window over which the first and second counts are determined, T. The indication of the second count can be calculated using Equation 3.

$$\text{Second Indication} = b/T \quad \text{(Eq. 3)}$$

The first count, the second count, the first indication, and the second indication can be determined computationally without actually generating the scatter plot 404 and without needing to physically draw or plot the points on the scatter plot 404.

At 506, AF is indicated for a valid window when the first and second indications are satisfied, such as by using the AF indication output 205. For example, when a window is not declared valid at 503, 609, the AF indication output 205 will not indicate AF for the invalid window.

Figure 7:
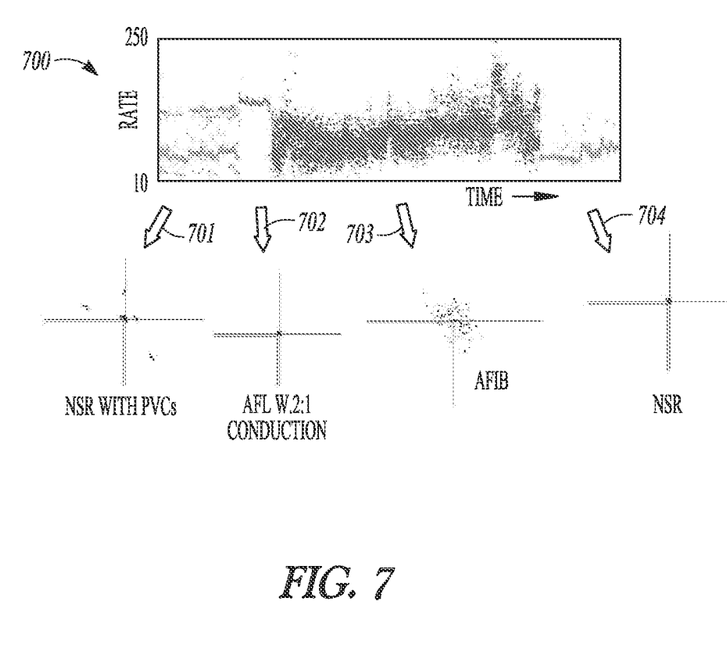
FIG. 7 illustrates pictorial examples of heart rhythm information and corresponding scatter plots.

FIG. 7 illustrates pictorial examples of heart rhythm information 700 and corresponding scatter plots. Four scatter plot signature examples are shown: a normal sinus rhythm (NSR) with premature ventricular contractions (PVCs) signature 701, an atrial flutter (Afl) with 2:1 conduction signature 702, an atrial fibrillation (AF or Afib) signature 703, and a normal sinus rhythm (NSR) signature 704.

A potential advantage of the present technique can include detecting atrial activity using ventricular information or from a ventricular location. For example, AF can be detected using only one ventricular lead, such as the lead 102. Parameters used with the present technique can be adjusted to ignore short bursts of AF, such as AF events lasting less than 50 cardiac cycles. The parameters can be configured to discriminate between cardiac rhythms, such as to discriminate atrial flutter with consistent conduction from AF. The present technique can be used to discriminate AF from one or more other cardiac rhythms, such as bigeminy and other premature ventricular contraction patterns. The parameters can be adjusted to accommodate pediatric rhythms, for example, such as by providing larger noise margins for the double-decrement criterion described above, such as to account for larger resting heart rate variability that can occur among pediatric populations.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided.

Example 1 can include subject matter (such as a system, a method, a means for performing acts, or a machine-readable medium including instructions that, when performed by the machine, cause the machine to perform acts, etc.) that can include an apparatus to detect atrial fibrillation. The apparatus can include a processor circuit. The processor circuit can include: (1) an input that can receive indications of pairs of first and second ventricular rate (or corresponding heart rate interval) changes of three temporally adjacent ventricular heart beats; (2) a first counter circuit, that can determine a first count of instances of the pairs in which a combined rate (or corresponding heart rate interval) change magnitude characteristic is less than at least one first criterion; (3) a second counter circuit, that can determine a second count of instances of the pairs in which both of the first and second ventricular rate (or corresponding heart rate interval) changes can be negative; and (4) an output to provide atrial fibrillation information using the first and second counts.

In Example 2, the subject matter of Example 1 can optionally be configured such that the second counter circuit can exclude instances of the pairs counted by the first counter circuit.

In Example 3, the subject matter of any one or any combination of Examples 1-2 can optionally be configured such that the second counter circuit can exclude instances of pairs of the first and second ventricular rate (or corresponding heart rate interval) changes wherein (1) a magnitude of the first ventricular rate (or corresponding heart rate interval) change can be less than a specified first threshold rate (or corresponding heart rate interval) change amount and (2) a magnitude of the second ventricular rate (or corresponding heart rate interval) change can be less than a specified second threshold rate (or corresponding heart rate interval) change amount.

In Example 4, the subject matter of one or any combination of Examples 1-3 can optionally be configured such that the input to receive indications of the pairs can receive the indications of the pairs over multiple windows, individual windows can comprise multiple temporally adjacent ventricular heart beats.

In Example 5, the subject matter of one or any combination of Examples 1-4 can optionally be configured such that the output can provide respective atrial fibrillation information for respective windows.

In Example 6, the subject matter of one or any combination of Examples 1-5 can optionally be configured such that the windows can be temporally non-overlapping and the individual windows can comprise the same duration.

In Example 7, the subject matter of one or any combination of Examples 1-6 can optionally be configured such that the processor circuit can declare ventricular beats to be valid based on occurrences of the ventricular heart beats at less than a specified threshold heart rate (or corresponding heart rate interval).

In Example 8, the subject matter of one or any combination of Examples 1-7 can optionally be configured such that the processor circuit can declare ventricular heart beats to be valid based on a specified signal noise criterion.

In Example 9, the subject matter of one or any combination of Examples 1-8 can optionally be configured such that the processor circuit can declare ventricular heart beats to be valid based on a dynamically determined signal morphological criterion.

In Example 10, the subject matter of one or any combination of Examples 1-9 can optionally be configured such that the input can receive the indications of the pairs over multiple windows, individual windows can comprise multiple temporally adjacent ventricular heart beats, and wherein the processor circuit can declare a window to be valid based on whether a number of the valid ventricular beats within the window exceeds a specified minimum number of valid ventricular beats; and the output can provide the atrial fibrillation information by determining the first and second counts using only windows that have been declared valid.

In Example 11, the subject matter of one or any combination of Examples 1-10 can optionally be configured such that the input can receive indications of pairs over multiple windows, individual windows can comprise multiple temporally adjacent ventricular heart beats, and wherein the output can provide the atrial fibrillation information using a first indication of the first count relative to: (1) a total number of instances of pairs in a window over which the first and second counts can be determined, less (2) the first count.

In Example 12, the subject matter of one or any combination of Examples 1-11 can optionally be configured such that the input can receive indications of pairs over multiple windows, individual windows can comprise multiple temporally adjacent ventricular heart beats, and wherein the output can provide the atrial fibrillation information using a second indication of the second count relative to the total number of instances of pairs in a window over which the first and second counts can be determined.

In Example 13, the subject matter of one or any combination of Examples 1-12 can optionally be configured such that the input can receive indications of pairs over multiple windows, individual windows can comprise multiple temporally adjacent ventricular heart beats, and wherein the processor circuit can determine the atrial fibrillation information using: a first indication of the first count relative to: (1) a total number of instances of pairs in a window over which the first and second counts can be determined, less (2) the first count; and a second indication of the second count relative to the total number of instances of pairs in a window over which the first and second counts can be determined.

Example 14 can include, or can be combined with the subject matter of one or any combination of Examples 1-13 to optionally include, subject matter (such as an apparatus, a method, a means for performing acts, or a machine-readable medium including instructions that, when performed by the machine, cause the machine to perform acts)

that can comprise: receiving, at a processor circuit, indications of pairs of first and second ventricular rate (or corresponding heart rate interval) changes of three temporally adjacent ventricular heart beats; determining, using the processor circuit, a first count of instances of the pairs in which a combined rate (or corresponding heart rate interval) change magnitude characteristic can be less than at least one first criterion; determining, using the processor circuit, a second count of instances of the pairs in which both of the first and second ventricular rate (or corresponding heart rate interval) changes can be negative; and determining, using the processor circuit, atrial fibrillation information using the first and second counts.

In Example 15, the subject matter of one or any combination of Examples 1-14 can optionally be configured such that the receiving the indications of the pairs comprises receiving the indications of the pairs over multiple windows, individual windows can comprise multiple temporally adjacent ventricular heart beats; and wherein, the determining the atrial fibrillation information includes determining respective atrial fibrillation information for respective windows; and wherein the determining the atrial fibrillation information includes: a first indication of the first count relative to: (1) a total number of instances of pairs in a window over which the first and second counts can be determined, less (2) the first count; and a second indication of the second count relative to the total number of instances of pairs in a window over which the first and second counts can be determined.

Example 16 can include, or can be combined with the subject matter of one or any combination of Examples 1-15 to optionally include, subject matter (such as an apparatus, a method, a means for performing acts, or a machine-readable medium including instructions that, when performed by the machine, cause the machine to perform acts) that can include an apparatus to detect atrial fibrillation. The apparatus can include a processor circuit. The processor circuit can include: (1) an input that can receive indications of pairs of first and second ventricular rate (or corresponding heart rate interval) changes of three temporally adjacent ventricular heart beats; (2) a first counter circuit that can determine a first count of instances of the pairs in which a combined rate (or corresponding heart rate interval) change magnitude characteristic can be less than at least one first criterion; (3) a second counter circuit that can determine a second count of instances of the pairs in which both of the first and second ventricular rate (or corresponding heart rate interval) changes can be negative; and (4) an output that can provide atrial fibrillation information using the first and second counts.

In Example 17, the subject matter of one or any combination of Examples 1-16 can optionally be configured such that the second counter circuit can exclude instances of the pairs counted by the first counter circuit.

In Example 18, the subject matter of one or any combination of Examples 1-17 can optionally be configured such that the second counter circuit can exclude instances of pairs of the first and second ventricular rate (or corresponding heart rate interval) changes wherein (1) a magnitude of the first ventricular rate (or corresponding heart rate interval) change can be less than a specified first threshold rate (or corresponding heart rate interval) change amount and (2) a magnitude of the second ventricular rate (or corresponding heart rate interval) change can be less than a specified second threshold rate (or corresponding heart rate interval) change amount.

In Example 19, the subject matter of one or any combination of Examples 1-18 can optionally be configured such that the input to receive indications of the pairs can receive the indications of the pairs over multiple windows, individual windows can comprise multiple temporally adjacent ventricular heart beats; and wherein the output can provide respective atrial fibrillation information for respective windows.

In Example 20, the subject matter of one or any combination of Examples 1-19 can optionally be configured such that the windows can be temporally non-overlapping and the individual windows can comprise the same duration.

In Example 21, the subject matter of one or any combination of Examples 1-20 can optionally be configured such that the processor circuit can: (1) declare ventricular heart beats to be valid based on: (i) occurrences of the ventricular heart beats at less than a specified threshold heart rate (or corresponding heart rate interval), (ii) a specified signal noise criterion, and (iii) a dynamically determined signal morphological criterion; (2) declare a window to be valid based on whether a number of the valid ventricular beats within the window exceeds a specified minimum number of valid ventricular beats; and (3) the output can provide the atrial fibrillation information by determining the first and second counts using only windows that have been declared valid.

In Example 22, the subject matter of one or any combination of Examples 1-21 can optionally be configured such that the processor circuit can determine the atrial fibrillation information using: a first indication of the first count relative to: (1) a total number of instances of pairs in a window over which the first and second counts can be determined, less (2) the first count; and a second indication of the second count relative to the total number of instances of pairs in a window over which the first and second counts can be determined.

Example 23 can include, or can be combined with the subject matter of one or any combination of Examples 1-22 to optionally include, subject matter (such as an apparatus, a method, a means for performing acts, or a machine-readable medium including instructions that, when performed by the machine, cause the machine to perform acts) that can include a medical system to detect atrial fibrillation. The system can include an ambulatory medical device (AMD) for use in a patient. The AMD can include an atrial fibrillation detection processor circuit. The atrial fibrillation detection processor circuit can include: (1) a detector circuit, that can comprise: (i) a heart beat sensing circuit configured that can sense indications of ventricular heart beats of the patient; (ii) a window determinator that can receive the indications of the heart beats over multiple windows, individual windows can comprise multiple temporally adjacent ventricular heart beats; (2) an input that can receive indications of pairs of first and second ventricular rate (or corresponding heart rate interval) changes of three temporally adjacent ventricular heart beats; (3) a first counter circuit that can determine a first count of instances of the pairs in which a combined rate (or corresponding heart rate interval) change magnitude characteristic can be less than at least one first criterion; (4) a second counter circuit that can determine a second count of instances of the pairs in which both of the first and second ventricular rate (or corresponding heart rate interval) changes can be negative; and (5) an output that can provide atrial fibrillation information using the first and second counts.

In Example 24, the subject matter of one or any combination of Examples 1-23 can optionally be configured such that the heart beat sensing circuit can declare ventricular heart beats to be valid based on validity criteria including: (1) occurrences of the ventricular heart beats at less than a specified threshold heart rate (or corresponding heart rate interval), (2) a specified signal noise criterion, and (3) a dynamically determined signal morphological criterion.

In Example 25, the subject matter of one or any combination of Examples 1-24 can optionally be configured such that the processor circuit can determine the atrial fibrillation information using: a first indication of the first count relative to: (1) a total number of instances of pairs in a window over which the first and second counts can be determined, less (2) the first count; and a second indication of the second count relative to the total number of instances of pairs in a window over which the first and second counts can be determined Example 26 can include, or can be combined with the subject matter of one or any combination of Examples 1-25 to optionally include, subject matter (such as an apparatus, a method, a means for performing acts, or a machine-readable medium including instructions that, when performed by the machine, cause the machine to perform acts) that can comprise receiving, at a processor circuit, indications of pairs of first and second ventricular rate (or corresponding heart rate interval) changes of three temporally adjacent ventricular heart beats; determining, using the processor circuit, a first count of instances of the pairs in which a combined rate (or corresponding heart rate interval) change magnitude characteristic can be less than at least one first criterion; determining, using the processor circuit, a second count of instances of the pairs in which both of the first and second ventricular rate (or corresponding heart rate interval) changes can be negative; and determining, using the processor circuit, atrial fibrillation information using the first and second counts.

In Example 27, the subject matter of one or any combination of Examples 1-26 can optionally be configured such that the determining the second count can exclude instances of the pairs included in the first count.

In Example 28, the subject matter of one or any combination of Examples 1-27 can optionally be configured such that the determining the second count can exclude instances of pairs of the first and second ventricular rate (or corresponding heart rate interval) changes wherein (1) a magnitude of the first ventricular rate (or corresponding heart rate interval) change can be less than a specified first threshold rate (or corresponding heart rate interval) change amount and (2) a magnitude of the second ventricular rate (or corresponding heart rate interval) change can be less than a specified second threshold rate (or corresponding heart rate interval) change amount.

In Example 29, the subject matter of one or any combination of Examples 1-28 can optionally be configured such that receiving the indications of the pairs can comprise receiving the indications of the pairs over multiple windows, individual windows can comprise multiple temporally adjacent ventricular heart beats; and wherein, the determining the atrial fibrillation information can include determining respective atrial fibrillation information for respective windows.

In Example 30, the subject matter of one or any combination of Examples 1-29 can optionally be configured such that the windows can be temporally non-overlapping and the size of each of the non-overlapping windows can comprise the same duration.

In Example 31, the subject matter of one or any combination of Examples 1-30 can optionally be configured such that ventricular heart beats can be declared to be valid based on occurring at less than a specified threshold heart rate (or corresponding heart rate interval), a specified signal noise criterion, and a dynamically determined signal morphological criterion; a window can be declared to be valid when a number of the valid ventricular beats within the window exceeds a specified minimum number of valid ventricular beats; and the atrial fibrillation information can be determined by determining the first and second counts using only windows that have been declared valid.

In Example 32, the subject matter of one or any combination of Examples 1-31 can optionally be configured such that ventricular heart beats can be declared to be valid based on: (1) occurring at less than a specified threshold heart rate (or corresponding heart rate interval), (2) a specified signal noise criterion, and (3) a dynamically determined signal morphological criterion; and the atrial fibrillation information can be determined by determining the first and second counts using only beats that have been declared valid.

In Example 33, the subject matter of one or any combination of Examples 1-32 can optionally be configured such that the atrial fibrillation information can be determined using a first indication of the first count relative to: (1) a total number of instances of pairs in a window over which the first and second counts can be determined, less (2) the first count.

In Example 34, the subject matter of one or any combination of Examples 1-33 can optionally be configured such that the atrial fibrillation information can be determined using a second indication of the second count relative to the total number of instances of pairs in a window over which the first and second counts can be determined.

In Example 35, the subject matter of one or any combination of Examples 1-34 can optionally be configured such that the atrial fibrillation information can be determined using: a first indication of the first count relative to: (1) a total number of instances of pairs in a window over which the first and second counts can be determined, less (2) the first count; and a second indication of the second count relative to the total number of instances of pairs in a window over which the first and second counts can be determined.

These examples can be combined in any permutation or combination.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Although certain examples and claims have been expressed in terms of heart "rate," (e.g., in beats per minute) it is understood that a corresponding heart rate interval (e.g., in milliseconds) is an equivalent indication of heart rate and should be considered to fall within the scope of the term "rate" recited in the claims.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus to detect atrial fibrillation in a window of temporally adjacent ventricular heart beats, the apparatus comprising:
a processor circuit, comprising:
an input configured to receive indications of pairs of first and second ventricular rate changes of three temporally adjacent ventricular heart beats of a window of temporally adjacent ventricular heart beats;
a first counter circuit configured to determine a first count of instances of the pairs in which a combined rate change magnitude characteristic in units of beats per minute (bpm) is less than at least one first criterion having a unit of bpm; and
a second counter circuit configured to determine a second count of instances of the pairs in which both of the first and second ventricular rate changes are negative;
wherein the processor circuit is configured to determine first and second indications of atrial fibrillation for the window of temporally adjacent ventricular heart beats, wherein the first indication comprises the first count relative to (1) a total number of instances of pairs in the window over which the first and second counts are determined less (2) the first count, and the second indication comprises the second count relative to the total number of instances of pairs in the window over which the first and second counts are determined, the processor circuit further comprising:
an output to provide the determined first and second indications of atrial fibrillation for the window of temporally adjacent ventricular heart beats.

2. The apparatus of claim 1, wherein the second counter circuit is configured to exclude instances of the pairs counted by the first counter circuit.

3. The apparatus of claim 2, wherein the second counter circuit is configured to exclude instances of pairs of the first and second ventricular rate changes wherein (1) a magnitude of the first ventricular rate change in units of bpm is less than a specified first threshold rate change amount having a unit of bpm and (2) a magnitude of the second ventricular rate change in units of bpm is less than a specified second threshold rate change amount having a unit of bpm.

4. The apparatus of claim 1, wherein the input configured to receive indications of the pairs is configured to receive the indications of the pairs over multiple windows of temporally adjacent ventricular heart beats; and
wherein the output is configured to provide the determined first and second indications of atrial fibrillation for respective windows.

5. The apparatus of claim 4, wherein the windows are temporally non-overlapping and the individual windows comprise the same duration.

6. The apparatus of claim 5, wherein the processor circuit is configured to:
declare ventricular heart beats to be valid based on:
occurrences of the ventricular heart beats at less than a specified threshold heart rate in units of bpm;
a specified signal noise criterion;
a dynamically determined signal morphological criterion; and
declare a window to be valid based on whether a number of the valid ventricular beats within the window exceeds a specified minimum number of valid ventricular beats; and
the output is configured to provide the determined first and second indications of atrial fibrillation for the respective windows by determining the first and second counts using only windows that have been declared valid.

7. The apparatus of claim 1, wherein the first indication comprises the first count (a) relative to the total number of instances of pairs in the window over which the first and second counts are determined (T) less the first count (a), a/T−a, and
wherein the second indication comprises the second count (b) relative to the total number of instances of pairs in the window over which the first and second counts are determined (T), b/T.

8. The apparatus of claim 1, comprising an ambulatory medical device for use in a patient, including the processor circuit, wherein the processor circuit includes:
a detector circuit, comprising:
a heart beat sensing circuit configured to sense indications of ventricular heart beats of the patient; and
a window determiner circuit configured to receive the indications of the heart beats over multiple windows of temporally adjacent ventricular heart beats.

9. A method of detecting atrial fibrillation in a window of temporally adjacent ventricular heart beats, the method comprising:
receiving, at a processor circuit, indications of pairs of first and second ventricular rate changes of three temporally adjacent ventricular heart beats of a window of temporally adjacent ventricular heart beats;
determining, using the processor circuit, a first count of instances of the pairs in which a combined rate change magnitude characteristic in units of beats per minute (bpm) is less than at least one first criterion having a unit of bpm;
determining, using the processor circuit, a second count of instances of the pairs in which both of the first and second ventricular rate changes are negative;
determining, using the processor circuit, first and second indications of atrial fibrillation for the window of temporally adjacent ventricular heart beats, wherein the first indication comprises the first count relative to (1) a total number of instances of pairs in the window over which the first and second counts are determined less (2) the first count, and the second indication comprises the second count relative to the total number of instances of pairs in the window over which the first and second counts are determined; and
outputting the first and second indications of atrial fibrillation for the window of temporally adjacent ventricular beats.

10. The method of claim 9, wherein the determining the second count excludes instances of the pairs included in the first count.

11. The method of claim 10, wherein the determining the second count excludes instances of pairs of the first and second ventricular rate changes in units of bpm wherein (1) a magnitude of the first ventricular rate change in units of bpm is less than a specified first threshold rate change amount having a unit of bpm and (2) a magnitude of the second ventricular rate change in units of bpm is less than a specified second threshold rate change amount having a unit of bpm.

12. The method of claim 9, wherein the receiving the indications of the pairs comprises receiving the indications of the pairs over multiple windows of temporally adjacent ventricular heart beats; and
wherein the outputting comprises outputting first and second indications of atrial fibrillation for respective windows.

13. The method of claim 12, wherein the windows are temporally non-overlapping and the size of each of the non-overlapping windows comprises the same duration.

14. The method of claim 13, comprising:
declaring ventricular heart beats to be valid based on occurring at less than a specified threshold heart rate in units of bpm, a specified signal noise criterion, and a dynamically determined signal morphological criterion; and
declaring a window to be valid when a number of the valid ventricular beats within the window exceeds a specified minimum number of valid ventricular beats,
wherein the outputting first and second indications of atrial fibrillation for the respective windows includes using only windows that have been declared valid.

15. The method of claim 9, comprising:
declaring ventricular heart beats to be valid based on:
(1) occurring at less than a specified threshold heart rate in units of bpm, (2) a specified signal noise criterion, and (3) a dynamically determined signal morphological criterion,
wherein determining first and second indications of atrial fibrillation includes using only beats that have been declared valid.

16. The method of claim 9, wherein the first indication comprises the first count (a) relative to the total number of instances of pairs in the window over which the first and second counts are determined (T) less the first count (a), a/T−a, and
wherein the second indication comprises the second count (b) relative to the total number of instances of pairs in the window over which the first and second counts are determined (T), b/T.

17. A system to detect atrial fibrillation in a window of temporally adjacent ventricular heart beats, the system comprising:
means for receiving indications of pairs of first and second ventricular rate changes of three temporally adjacent ventricular heart beats of a window of temporally adjacent ventricular heart beats;
means for determining a first count of instances of the pairs in which a combined rate change magnitude characteristic in units of beats per minute (bpm) is less than at least one first criterion having a unit of bpm;
means for determining a second count of instances of the pairs in which both of the first and second ventricular rate changes are negative;
means for determining first and second indications of atrial fibrillation for the window of temporally adjacent ventricular heart beats, wherein the first indication comprises the first count relative to (1) a total number of instances of pairs in the window over which the first and second counts are determined less (2) the first count, and the second indication comprises the second count relative to the total number of instances of pairs in the window over which the first and second counts are determined; and
means for outputting the first and second indications of atrial fibrillation for the window of temporally adjacent ventricular beats.

18. The system of claim 17, comprising:
means for determining validity of the window,
wherein means for determining first and second indications of atrial fibrillation comprises only for windows that have been declared valid,
wherein the first indication comprises the first count (a) relative to the total number of instances of pairs in the window over which the first and second counts are determined (T) less the first count (a), a/T−a, and
wherein the second indication comprises the second count (b) relative to the total number of instances of pairs in the window over which the first and second counts are determined (T), b/T.

\* \* \* \* \*